(12) United States Patent
Shimizu et al.

(10) Patent No.: US 9,782,745 B2
(45) Date of Patent: Oct. 10, 2017

(54) METAL ORGANIC FRAMEWORK, PRODUCTION AND USE THEREOF

(71) Applicant: UTI LIMITED PARTNERSHIP, Calgary (CA)

(72) Inventors: George Shimizu, Calgary (CA); Ramanathan Vaidhyanathan, Calgary (CA); Simon Iremonger, Calgary (CA); Kyle Deakin, Calgary (CA); Jian-Bin Lin, Calgary (CA); Karl W. Dawson, Calgary (CA)

(73) Assignee: UTI Limited Partnership, Calgary, Alberta (CA)

( * ) Notice: Subject to any disclaimer, the term of this patent is extended or adjusted under 35 U.S.C. 154(b) by 0 days.

(21) Appl. No.: 14/775,267

(22) PCT Filed: Mar. 11, 2014

(86) PCT No.: PCT/CA2014/000204
§ 371 (c)(1),
(2) Date: Sep. 11, 2015

(87) PCT Pub. No.: WO2014/138878
PCT Pub. Date: Sep. 18, 2014

(65) Prior Publication Data
US 2016/0016148 A1 Jan. 21, 2016

Related U.S. Application Data

(60) Provisional application No. 61/776,223, filed on Mar. 11, 2013.

(51) Int. Cl.
*B01D 53/02* (2006.01)
*B01J 20/22* (2006.01)
*B01J 20/28* (2006.01)
*C01B 31/20* (2006.01)
*C07F 3/06* (2006.01)

(52) U.S. Cl.
CPC ............ *B01J 20/226* (2013.01); *B01D 53/02* (2013.01); *B01J 20/2808* (2013.01); *B01J 20/28057* (2013.01); *C01B 31/20* (2013.01); *C07F 3/06* (2013.01); *B01D 2253/204* (2013.01); *B01D 2256/245* (2013.01); *B01D 2257/504* (2013.01); *B01D 2258/0283* (2013.01); *Y02C 10/04* (2013.01); *Y02C 10/06* (2013.01); *Y02C 10/08* (2013.01); *Y02P 20/152* (2015.11)

(58) Field of Classification Search
CPC ............ B01D 53/02; B01D 2253/204; B01D 2256/245; B01D 2257/504; B01D 2258/0283; B01J 20/226; B01J 20/28057; B01J 20/2808; C01B 31/20; C07F 3/06; Y02C 10/04; Y02C 10/06; Y02C 10/08; Y02P 20/152

USPC .............................. 95/90, 139, 902; 502/401
See application file for complete search history.

(56) References Cited

U.S. PATENT DOCUMENTS

| 8,796,462 | B2 * | 8/2014 | Li | B01D 53/02 548/101 |
|---|---|---|---|---|
| 2010/0132549 | A1 * | 6/2010 | Yaghi | B01D 53/02 95/128 |
| 2012/0118153 | A1 * | 5/2012 | Omary | B01D 53/02 95/143 |
| 2012/0186449 | A1 * | 7/2012 | Yaghi | C07D 249/04 95/90 |
| 2013/0012717 | A1 * | 1/2013 | Trukhan | C07F 3/06 548/101 |
| 2015/0158012 | A1 * | 6/2015 | Ramanathan | B01J 20/226 95/96 |

OTHER PUBLICATIONS

Zhai et al., "Coligand modulated six-, eight-, and ten-connected Zn/Cd-1,2,4-triazolate frameworks based on mono-, bi-, tri-, penta-, and heptanuclear cluster units", Cryst. Growth Des., 2007, 7/11, 2332-2342.*
Lin et al., "Pillaring Zn-triazolate layers with flexible aliphatic dicarboxylates into three-dimensional metal-organic frameworks", Cryst. Growth Des., 2008, 8(10), 3673-3679.*
Erucar, et al.. (Feb. 2013) "High $CO_2$ Selectivity of an Amine-Functionalized Metal Organic Framework in Adsorption-Based and Membrane-Based Gas Separations" *Ind. Eng. Chem Res.*, 52(9), pp. 3462-3472.
European Search Report corresponding to European Application No. 14 764170.8, dated Nov. 21, 2016.
Garcia-Couceiro, et al. (2006) "Rational Design of 2D Magnetic Metal-Organic Coordination Polymers Assembled from Oxalato and Dipyridyl Spacers," *Cryst. Growth Des*. 6(08), pp. 1839-1847.
Garcia-Teran, et al. (2004) "One-Dimensional Oxalato-Bridged Cu(II), Co(II), and Zn(II) Complexes with Purine and Adenine as Terminal Ligands," *Inorganic Chem*. 43(18), pp. 5761-5770.
Ghosh, et al. (2004) "Reactivity of Pyridine-2,4,6-tricarboxylic Acid toward Zn(II) Salts under Different Reaction Conditions," *Inorganic Chem*. 43(18), pp. 5495-5497.
International Search Report and Written Opinion corresponding to International Application No. PCT/CA2014/000204, mailed Jun. 11, 2014.
Li, et al. (2011) "Structure Modulation in Zn(II)-1,4-Bis(imidazol-1-yl)benzene Frameworks by Varying Dicarboxylate Anions," *Cryst. Growth Des*. (2012), 12(1), pp. 189-196.
Li, et al. (Jul. 2013) "One-step fabrication of ZIF-8/polymer composite spheres by a phase inversion method for gas adsorption," *Colloid Polym. Sci.*, 291(11), pp. 2711-2717.

(Continued)

*Primary Examiner* — Frank Lawrence
(74) *Attorney, Agent, or Firm* — Lathrop Gage LLP (57) ABSTRACT

Metal-organic framework (MOF) materials particularly useful for adsorbing $CO_2$. More specifically the MOF has pores and comprises zinc ions, oxalate, and a cycloazocarbyl compound. A preferred cycloazocarbyl compound is 1,2,4-triazolate. Methods for making the porous MOH and methods for using the porous MOH for adsorbing $CO_2$.

45 Claims, 4 Drawing Sheets

(56) References Cited

OTHER PUBLICATIONS

Park, et al. (2007). "Synthesis and Structural Determination of Four Novel Metal-Organic Frameworks in a Zn-3-Amino-1,2,4-Triazole System." *Cryst. Growth Des.*, 7(7), pp. 1343-1349.
Qian, et al. (Aug. 2013) "One-step Preparation of Macroporous Polymer Particles with Multiple Interconnected Chambers: A Candidate for Trapping Biomacromolecules." Angew. Chem., 52(40), pp. 10625-10629.
Ren, et al. (2011). "Synthesis and characterization of two new triazolate-aliphatic dicarboxylate bridged Zn(II) coordination polymers based on 2D layer motifs with different crystal packing." *Inorg. Chim. Acta*, 373(1), pp. 79-84.
Rodriquez-Dieguez, et al. (2006) "[ZnII(polyox)(pmtz),,]: the first polyoxalate-containing coordination polymer from an unforeseen chemical rearrangement of 5-pyrimidyltetrazole under hydrothermal conditions," *Chem. Comm.* 39, pp. 4140-4142.
Thirugnanam, (Apr. 2013). "Effect of Polymers (PEG and PVP) on Sol-Gel Synthesis of Microsized Zinc Oxide." J. Nanomater., ID: 362175, 7 pages.
Su, et al. (Oct. 2003). "Exceptionally Stable, Hollow Tubular Metal-Organic Architectures: Synthesis, Characterization, and Solid-State Transformation Study." J. Am. Chem. Soc., 126(11), 2004, pp. 3576-3586.
Vaidhyanathan, et al. (2009) "An amine-functionalized metal organic framework for preferential CO2 adsorption at low pressures," *Chem. Comm.* 35, pp. 5230-5232.
Vaidhyanathan, et al. (2010) "Direct Observation and Quantification of $CO_2$ Binding Within an Amine-Functionalized Nanoporous Solid," *Science*, 330(6004), pp. 650-653.
Vaidhyanathan, et al. (Dec. 2012) "Competition and Cooperativity in Carbon Dioxide Sorption by Amine-Functionalized Metal-Organic Frameworks," *Angew. Comm.*, 51(8), pp. 1826-1829.
Yuan, et al. (Nov. 2012) "Effect of pH/metal ion on the structure of metal-organic frameworks based on novel bifunctionalized ligand 4,-carboxy-4,2':6'/4"-terpyridine," *Cryst. Growth Des.*, 15(7), 2013, pp. 1460-1467.
Zheng, et al. (2007) "Poly[bis($\mu_3$-3-amino-1,2,4-triazolato)-($\mu_2$-glutarato)dizinc(II)]," *Acta Cryst.*, E63, pp. m1252-m1253.

\* cited by examiner

METAL ORGANIC FRAMEWORK, PRODUCTION AND USE THEREOF

CROSS-REFERENCE TO RELATED APPLICATIONS

This application is a U.S. National Stage application under 35 U.S.C. 371 of PCT/CA2014/000204, filed in English on Mar. 11, 2014, which claims the benefit of U.S. provisional patent application 61/776,223, filed Mar. 11, 2013. Each of these applications is incorporated by reference herein in its entirety.

BACKGROUND OF THE INVENTION

This invention relates to porous metal-organic frameworks, and to methods of their production and use.

Capturing harmful greenhouse gases, particularly $CO_2$, from industrial effluents could contribute to the minimization of global $CO_2$ content. Porous solids capable of adsorbing $CO_2$ on their surfaces (physisorbing) have been identified as a possible alternative for the existing amine scrubbing process used for industrial $CO_2$ capture. In amine scrubbing, the $CO_2$ is chemically bonded (chemisorbed) to the amine to form a carbamate salt; regeneration of the sorbent requires cleavage of this bond. For capture from flue gas, two major challenges are to capture $CO_2$ at extremely low (0.1 bar) partial pressure and to exclude other major components such as $N_2$ and $H_2O$. Importantly, compared to a chemically bonded entity, the weaker interaction of physisorbed $CO_2$ requires less energy to release the gas for future use or storage. Beyond the greater strength of the CO2 binding interaction, the amine scrubbing process employs an aqueous amine solution so the total energy cost to release $CO_2$ and regenerate the sorbent includes heating the entire solution and water has a very high specific heat capacity. It is typically estimated that, to implement amine scrubbing at a coal-fired power plant, the plant would need to increase energy production by 30-40% to compensate for the $CO_2$ capture. The main benefit of a $CO_2$ physisorbing solid would be to reduce the $CO_2$ liberation energy due both to a weaker interaction of the gas and the absence of a supporting aqueous solution.

Metal organic frameworks (MOFs)/porous coordination polymers (PCPs) are a class of network solids composed of organic spacers linking metal ions or metal ion clusters. They possess ordered (crystalline) structures permeated by pores able to adsorb gas molecules. The regularity of these materials makes them amenable to structural characterization by X-ray diffraction techniques. Detailed knowledge of pore size, shape and surface chemistry can provide greater insights to interpretation of adsorption isotherms. In principle, researchers are able to establish structure activity relationships and better design next generation materials.

Water stability has been shown to be a weakness for many MOFs as even low amounts of atmospheric moisture can compromise the order and the porosity. Some very stable Zr carboxylate MOFs have been reported recently (MIL-140 series, UiO-66 series) but merging high capacity with high stability is still a challenge. Also, with regards to implementation of a capture material, it is difficult to generalize a set of ideal characteristics of the sorbent (pore sizes, heat of adsorption for $CO_2$, shape of isotherm). This is because the characteristics of the ideal sorbent would be specific to the capture system into which it is implemented, broadly pressure-swing, temperature-swing, or vacuum-swing technology. Moreover, the conditions for regeneration would best be dictated by the availability of low cost energy at the specific capture site and this factor would influence selection of the sorbent.

SUMMARY OF THE INVENTION

Disclosed herein is a metal-organic framework (MOF). The MOF has pores and the framework includes zinc ions, oxalate, and a cycloazocarbyl compound.

The example describes a particular compound that has been shown to be capable of adsorbing gases, particularly carbon dioxide, and to do so to a greater extent than it adsorbs nitrogen. The compound has also been shown to be thermally stable, establishing its feasibility for use as a carbon capture agent.

In embodiments, the cycloazocarbyl compound of the MOF is at least bidentate, having 2, 3 or 4 nitrogen atoms, typically as part of a 5-membered ring. Examples of such are imidazolates, triazolates and tetrazolates. Particular embodiments include 1,2,4-triazolate. Others are 1H-1,2,4-triazolate-1-carboxamidine, 3-amino-1,2,4-triazolate, imidazolate, 4-fluoroimidazolate, 2-methyl-imidazolate and 1,2,3,4-tetrazolate. In a specific embodiment, the cycloazocarbyl group is a group other than the 3-amino-1,2,4-triazolate. In a preferred embodiment, the cycloazocarbyl group is 1,2,4-triazolate.

A preferred zinc ion of MOFs described herein is $Zn^{2+}$.

Also described are methods for preparing a porous metal organic framework (MOF), methods for the separation of carbon dioxide from a gas mixture, and methods of absorbing carbon dioxide, storing the carbon dioxide, or absorbing and storing the carbon dioxide.

DETAILED DESCRIPTION OF THE INVENTION

The invention relates to metal-organic framework (MOF) material particularly useful for adsorbing $CO_2$. More specifically the MOF has pores and comprises zinc ions, oxalate, and a cycloazocarbyl compound. In an embodiment, the cycloazocarbyl compound is at least bidentate. In an embodiment, the ring of the cycloazocarbyl compound is a 5-membered ring having 2, 3 or 4 nitrogen atoms. In an embodiment, the cycloazocarbyl compound is an imidazolate, triazolate or tetrazolate. In an embodiment, the cycloazocarbyl compound is a 1,2,4-triazolate. In an embodiment, the cycloazocarbyl compound is selected from the group consisting of 1H-1,2,4-triazolate-1-carboxamidine, 3-amino-1,2,4-triazolate, imidazolate, 4-fluoroimidazolate, 2-methyl-imidazolate and 1,2,3,4-tetrazolate. In an embodiment, the cycloazocarbyl compound is a compound other than 3-amino-1,2,4-triazolate. In a specific embodiment, the cyclocarbyl compound is 1,2,4-triazolate. In specific embodiments the zinc ion is $Zn^{2+}$.

The preferred MOF of the invention has pores. In an embodiment, pore size ranges from 0.3 to 2 nm. MOF of the invention can have pore size ranging in nm from 0.4 to 1.9, from 0.5 to 1.8, from 0.6 to 1.7, or from 0.7 to 1. In specific embodiments, MOF of the invention can have pore size in nm or about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9 or about 2.0.

When the cycloazocarbyl compound is 1,2,4-triazolate, and particularly when made with $Zn^{2+}$, in an embodiment, the MOF has a powder X-ray diffraction pattern having the highest intensity diffraction peak in the range $10°<2\theta<15°$ with Cu Kα radiation.

Figure 1:
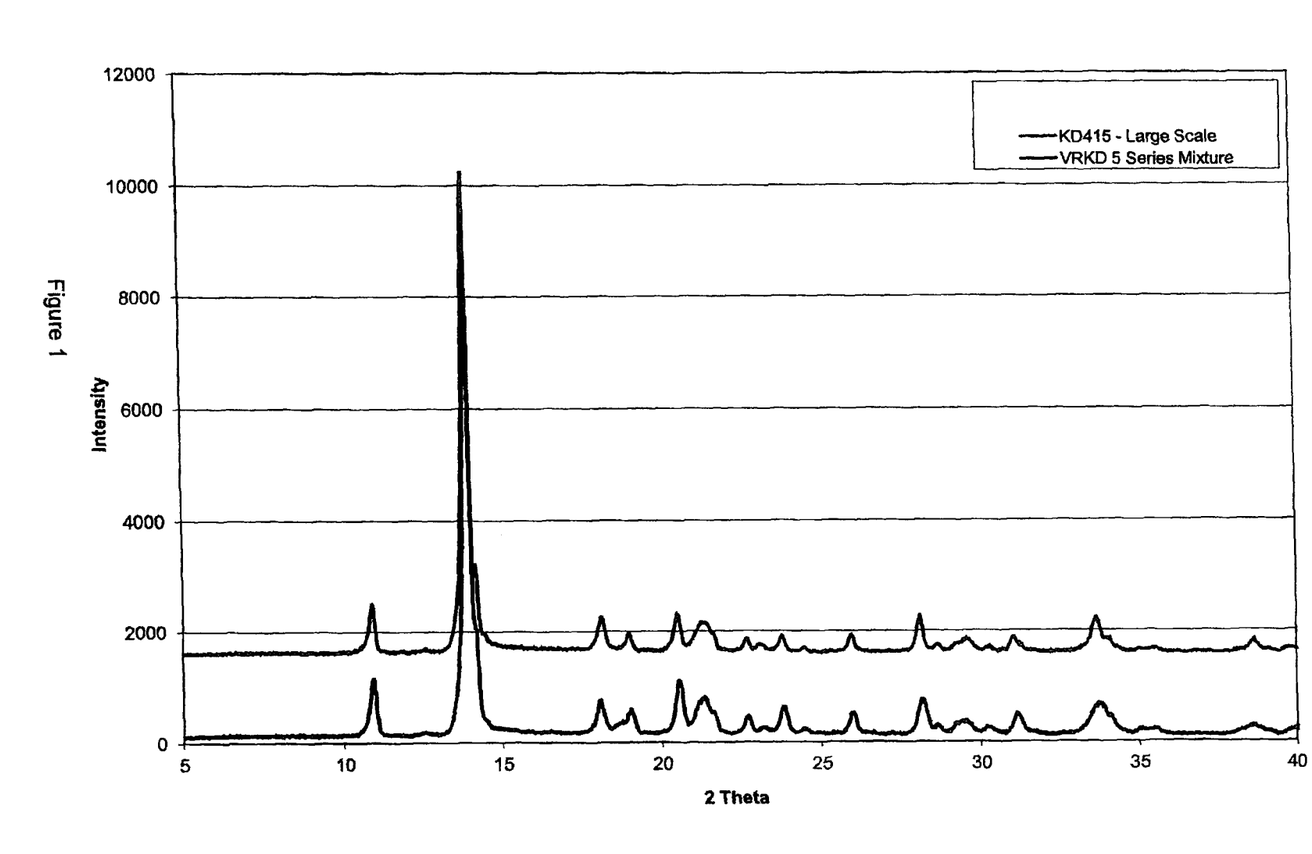
FIG. 1 shows the X-ray diffraction pattern of two batches of the MOF material obtained as described in the Example. The intensity (Ln(Counts)) is shown as a function of the 2Θ scale.

In a specific embodiment, a preferred MOF has the PXRD pattern substantially as shown in FIG. 1.

In a specific embodiment, the MOF is in the form of a powder having a Langmuir surface of at least 450 $m^2/g$ determined according to a 77K nitrogen gas isotherm fit to a Langmuir model.

In a specific embodiment, the invention comprises an MOF of the invention comprising an adsorbed gas. In a preferred embodiment the adsorbed gas is carbon dioxide. In a specific embodiment, the MOF has pores and comprises zinc ions, oxalate, and a 1,2,4-triazolate compound and further comprises an adsorbed gas, particularly $CO_2$.

In an embodiment, the invention relates to metal-organic framework (MOF) comprising a plurality of cores, each core comprising a zinc ion coordinately bound to at least one at least bidentate cycloazocarbyl compound and at least one oxalate, wherein the at least one at least bidentate cycloazocarbyl compound and the at least one oxalate are coordinately bound to the zinc ion of an adjacent core, wherein the plurality of linked cores defines pores within the framework. In specific embodiments, a preferred cycloazocarbyl compound is 1,2,4-triazolate. In a specific embodiment, there are two of said at least bidentate cycloazocarbyl compounds coordinately bound to the zinc ion of each said core. In a specific embodiment, there are two carboxylate oxygens of said oxalate coordinately bound to the zinc ion of each core. In a specific embodiment, the two carboxylate oxygens are covalently bound to vicinal carbon atoms of the oxalate. In an embodiment, in the MOF the other of the two carboxylate oxygens are coordinately bound to the zinc ion of an adjacent core. In a specific embodiment, the cycloazocarbyl compound is tridentate and each cycloazocarbyl compound is coordinately bound to zinc ions of three adjacent cores. In a specific embodiment, the cycloazocarbyl compound is 1,2,4-triazolate. In a specific embodiment, the plurality of cores of the MOF is homogeneous. The invention further relates to the forgoing MOF further comprising an adsorbed species, particularly where the adsorbed species is a gas and more particularly where the gas is $CO_2$.

In an embodiment, the invention relates to a metal organic framework (MOF) comprising a core of formula I:

wherein each $M^1$, $M^2$ and $M^3$ is $Zn^{2+}$
$XR^1$ is selected from the group consisting of N and $CR^3$;
and at least one of $R^2$ and $R^3$ is H, and the other of $R^2$ and $R^3$ is selected from the group consisting of H, $-NH_2$, optionally substituted ($C_1$-$C_{10}$)alkyl, optionally substituted ($C_1$-$C_{10}$)alkenyl, optionally substituted ($C_1$-$C_{10}$) alkynyl, optionally substituted ($C_1$-$C_{10}$)heteroalkyl, optionally substituted ($C_1$-$C_{10}$)heteroalkenyl, optionally substituted ($C_1$-$C_{10}$)heteroalkynyl, optionally substituted cycloalkyl, optionally substituted cycloalkenyl, optionally substituted aryl, optionally substituted heterocycle. In a specific embodiment, when X is C—$NH_2$ ($R_3$ is —$NH_2$), then $R_2$ is a group other than hydrogen. In a specific embodiment, when X is C—H ($R_3$ is —H), $R_2$ is H.

In an embodiment, the invention provides a MOF wherein the core is of formula II:

wherein, for each Y-$L^1$-Y, Y-$L^2$-Y and Y-$L^3$-Y,
(i) Y is an oxygen atom, and each $L^1$, $L^2$ and $L^3$ is independently selected from the group consisting of —C(O)C(O)—, —C(S)C(S)—, —C(O)$CH_2$$CH_2$C (O)—, —C(O)(CH$_2$)$_3$C(O)—, —C(O)(CH$_2$)$_4$C(O)—,
—C(O)CF$_2$CF$_2$C(O)—, —C(O)(CF$_2$)$_3$C(O)—,
—C(O)(CF$_2$)$_4$C(O)—, and or
(ii) one, two or three of Y-L$^1$-Y, Y-L$^2$-Y and Y-L$^3$-Y is —SC(O)C(O)S—Y and the other of Y-L$^1$-Y, Y-L$^2$-Y and Y-L$^3$-Y is as defined in paragraph (i) and X, R$^1$, R$^3$ and R$^2$ are as defined for formula I.

In an embodiment, the invention provides a MOF wherein the core is of formula III:

(III)

wherein Y, L$^{1-3}$, M$^{1-3}$, X, R$^{1-3}$ are as defined in Formulas I and II and each Z is, independently of each other Z, as defined for Y-L$^1$-Y in paragraph (i) or (ii) (Formula II) in which the atom represented by a first Y thereof is coordinated to M$^1$, M$^2$ and M$^3$, respectively, and the atom represented by the second Y is coordinated to a metal atom of an adjacent core of the MOF. In a specific embodiment, each of M$^1$, M$^2$ and M$^3$ is further coordinated to first and second nitrogen atoms in the rings of first and second neighboring polyazolate groups, a polyazolate being a cycloazocarbyl molecule containing three or four nitrogen atoms in its ring, and taking the form of a triazolate or tetrazolate as a constituent of a MOF.

In an embodiment, the invention provides a porous, metal-organic framework (MOF) material comprising zinc ions, oxalate, and a cycloazocarbyl compound. In a specific embodiment, the cycloazocarbyl compound is a 1,2,4 triazolate.

In an embodiment, the invention provides a metal-organic framework (MOF) comprising a plurality of cores, each core comprising a zinc ion coordinately bound to at least one at least bidentate cycloazocarbyl compound and at least one oxalate, wherein the at least one at least bidentate cycloazocarbyl compound and the at least one oxalate is coordinately bound to the zinc ion of an adjacent core, wherein the plurality of linked cores defines pores within the framework.

In an embodiment, the invention provides a material comprising at least one metal-organic framework (MOF) material, wherein the MOF material has pores and comprises zinc ions, oxalate, and a cycloazocarbyl compound.

The invention also relates to a method for preparing a porous metal organic framework (MOF) comprising at least an oxalate and a cycloazocarbyl compound coordinated to at least one zinc ion, which comprises the step of combining a zinc oxalate compound and the cycloazocarbyl compound to form a reaction mixture; and reacting the compounds in the reaction mixture at a selected temperature. The reacting step can be carried out in the presence of water, an organic solvent or a mixture thereof. In a specific embodiment, the solvent employed in the reaction is a mixture of water and organic solvent. In an embodiment, the mixture of water and organic solvent is miscible. In an embodiment, the organic solvent is or comprises an alcohol. In an embodiment the reacting step is carried out in the presence of water and at least one lower (C1-C4) alcohol. In an embodiment, the reacting step is carried out in the presence of water and an alcohol. In an embodiment, the ratio of water:alcohol (v/v) is between about 1:10 and 10:1. More specifically, the ratio of water:alcohol is or 1:10 and 5:1, or 1:5 and 4:1, or 1:4 and 3:1, or 1:4 and 2:1, of 1:3 and 2:1 or 1:3 and 1:1, or the ratio of water:alcohol (v/v) is about 5:6, or about 3:6, or about 2:3. In an embodiment, the alcohol is ethanol, propanol (various isomers including isopropanol) or butanol. In an embodiment, the alcohol is methanol and the ratio of water:methanol is 1:1 to 1:10 or more specifically 2:3 to 1:10. In a specific embodiment, the solvent employed is other than methanol. In a specific embodiment, the solvent is other than water.

In a specific embodiment, a useful MOH of this invention can be prepared by initial mixing of the Zn$^{2+}$, oxalate, and cycloazocarbyl in methanol, removal of methanol by evaporation, followed by treatment with water, followed by drying and heating of the material, particularly heating of 100-150° C. under reduced pressure. In a specific embedment, the cycloazocarbyl compound is 1,2,4-triazolate.

In specific embodiment, zinc oxalate is employed as a starting material in the preparation of the MOF. Use of Zn(NO$_2$)$_2$, ZnCl$_2$ or ZnSO$_4$ is not preferred. Use of these starting materials can lead to products which are not porous. An alternative to the use of zinc oxalate is the use of Zn carbonate, e.g., basic Zn carbonate, with addition of oxalic acid, where the components are allowed to react prior to addition of the cycloazocarbyl compound.

In specific embodiments, the reaction is carried out in the absence of water in methanol, ethanol, propanol or butanol (including isopropanol).

In specific embodiments, the reaction is carried out at a selected temperature in the range from 130° C. to 230° C. More specifically, the reaction can be carried out at a temperature in the following ranges: 140° C. to 220° C., or 150° C. to 230° C., or 150° C. to 220° C., or 150° C. to 210° C., or 160° C. to 210° C., or 160° C. to 200° C., or 170° C. to 190° C. More specifically, the reaction can be carried out at the following temperatures: about 130° C., or about 140° C., or about 150° C., or about 160° C., or about 170° C., or about 180° C., or about 190° C., or about 200° C., or about 210° C., or about 220° C., or about 230° C.

In a specific embodiment of the method, the reaction mixture is formed at a mixing temperature that is less than the selected temperature. In an embodiment, the method further comprises the step of ramping the temperature from the mixing temperature to the selected temperature. In a specific embodiment, the ratio of the reaction time to the ramping time is at least 2, or is at least 3, or is at least 4, or is at least 5 or is at least 6.

In the preparation method of the invention, the cycloazocarbyl compound can be selected from an imidazole, a triazole or a tetrazole. In a preferred embodiment, the cycloazocarbyl compound is a triazole and more specifically is an unsubstituted triazole and yet more specifically is an unsubstituted 1,2,4 triazole. More specifically the triazole is 1H-1,2,4-triazolate or 4H-1,2,4-triazolate.

In a specific embodiment, the molar ratio of $Zn^{2+}$:oxylate: carboazocarbyl compound in the MOF is 1:1:1. In a preferred embodiment, a molar excess of the carboazocarbyl compound is added during synthesis of the MOF compared to the oxalate ligand. More specifically the carboazocarbyl compound is added at at least a 2-fold molar excess over the oxalate. In an embodiment, $Zn^{2+}$ is added in an equimolar amount to oxalate. More specifically, the carboazocarbyl compound is added at a molar ration of 2:1 to 5:1 relative to oxalate. In a specific embodiment, in the preparation method the molar ratio of $Zn^{2+}$:oxylate:carboazocarbyl compound is 1:1:2 to 1:1:5 in the preparation reaction mixture.

In an embodiment, the method for the production of a porous MOF material comprises reaction of zinc oxalate with the at least one at least bidentate organic compound which can bind to the metal by coordination.

In specific embodiment, the preparation method proceeds at atmospheric pressure. However, it will be appreciated that the reaction can be adapted to use of higher than atmospheric pressure, for example, with modification of temperature. In a specific embodiment, the reaction proceeds with heating. In specific embodiments, the reaction proceeds at a temperature of at least 80° C., or at least 90° C., or at least 100° C., or at least 110° C., or at least 120° C., or at least 130° C., or at least 140° C., or at least 150° C., or at least 160° C., or at least 170° C., or at least 180° C.

In a specific embodiment, the reaction proceeds for at least 2 hours. More specifically, the reaction can proceed for or at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 hours.

After the reaction, the MOF material formed can be subsequently treated with an organic solvent, for example an alcohol.

In an embodiment, the invention provides a method for the separation of carbon dioxide from a gas mixture containing carbon dioxide comprising the steps of (a) contacting the gas mixture with at least one sorbent comprising a porous MOF of this invention. In a specific embodiment, the MOF comprises a 1,2,4, triazole compound.

In a specific embodiment, the method is applied to a gas mixture containing in addition to carbon dioxide at least one gas selected from the group consisting of nitrogen, oxygen, methane, hydrogen, water vapor, carbon monoxide, hydrogen sulfide, sulfur dioxide, nitrogen dioxide, and any mixture of the foregoing. More specifically, the gas mixture contains at least two gases in addition to $CO_2$. In an embodiment, the gas mixture contains water vapor. In a specific embodiment, the gas mixture is selected from the group consisting of natural gas, air, shale gas, and flue gas. In a specific embodiment, the natural gas, air, shale gas, or flue gas contains water vapor.

In a specific embodiment, the porous metal-organic framework material used in the method is in the form of a powder. In an embodiment, the powder has a Langmuir surface of at least 450 $m^2/g$ determined according to the Langmuir sorption model applied to a nitrogen sorption isotherm at 77K.

In a specific embodiment, the contacting step is carried out at a temperature ranging from 50° C. to 200° C. In more specific embodiments, the contacting step is carried out at a temperature ranging from 60° C. to 190° C., or from 70° C. to 180° C., or from 80° C. to 180° C., or from 90° C. to 180° C., or from 100° C. to 170° C. In specific embodiments, the contacting step is carried out at a temperature about 50, about 60, about 70, about 80, about 90, about 100, about 110, about 120, about 130, about 140, about 150, about 160, about 170, about 180, about 190 or 200° C.

In a specific embodiment of the method, the partial pressure of $CO_2$ in the gas ranges from 0.001 atm to 200 atm. In more specific embodiments, the partial pressure of $CO_2$ in the gas ranges from 0.01 to 200 atm, from 0.1 to 150 atm, from 0.1 to 100 atm, from 1 to 50 atm. In a more specific embodiment, the partial pressure of $CO_2$ in the gas ranges from 0.05 atm to 1 atm or 0.05 to 0.5 atm. In more specific embodiments, the partial pressure of $CO_2$ in the gas is about 0.001, about 0.01, about 0.1, about 1, about 10, about 20, about 30, about 40, about 50, about 60, about 70, about 80, about 90, about 100, about 110, about 120, about 130, about 140, about 150, about 160, about 170, about 180, about 190, about 200 atm, or an intermediate range between any of the foregoing.

The invention also provides a method of absorbing carbon dioxide, storing the carbon dioxide, or absorbing and storing the carbon dioxide, the method comprising contacting a gas containing $CO_2$ with an MOF of this invention under conditions suitable for absorption of the carbon dioxide. In a specific embodiment of this method, the partial pressure of $CO_2$ in the gas ranges from 0.001 atm to 200 atm. In more specific embodiments, the partial pressure of $CO_2$ in the gas ranges from 0.01 to 200 atm, from 0.1 to 150 atm, from 0.1 to 100 atm, from 1 to 50 atm. In a more specific embodiment, the partial pressure of $CO_2$ in the gas ranges from 0.05 atm to 1 atm or 0.05 to 0.5 atm. In more specific embodiments, the partial pressure of $CO_2$ in the gas is about 0.001, about 0.01, about 0.1, about 1, about 10, about 20, about 30, about 40, about 50, about 60, about 70, about 80, about 90, about 100, about 110, about 120, about 130, about 140, about 150, about 160, about 170, about 180, about 190, about 200 atm, or an intermediate range between any of the foregoing.

The invention further relates to a material comprising at least one metal-organic framework (MOF), wherein the MOF has pores and comprises zinc ions; an anionic compound selected from $[B_{12}H_{12}]^{2-}$, $[B_{12}F_{12}]^{2-}$, $[SiF_6]^{2-}$, $[PF_6]^{-}$, 1,2-dithiooxalic acid and its anions, 1,1-dithoxalic acid and its anions, succinic acid and its anions, glutaric acid and its anions, adipic acid and its anions, 2-fluoroterephthalic acid and its anions, tetrafluorosuccinic acid and its anions, hexafluoroglutaric acid and its anions, and octafluoroadipic acid and its anions; and a cycloazocarbyl compound. In an embodiment, the cycloazocarbyl compound is a 5-membered ring having 2, 3 or 4 nitrogen atoms. In an embodiment, the cycloazocarbyl compound is an imidazolate, triazolate or tetrazolate. In an embodiment, the cycloazocarbyl compound is a1,2,4-triazolate. In other embodiments, the cycloazocarbyl compound is selected from the group consisting of 1H-1,2,4-triazolate-1-carboxamidine, 3-amino-1,2,4-triazolate, imidazolate, 4-fluoroimidazolate, 2-methyl-imidazolate and 1,2,3,4-tetrazolate. In an embodiment, the cycloazocarbyl compound is a compound other than 3-amino-1,2,4-triazolate. More specifically the zinc ion is $Zn^{2+}$. In specific embodiments, the MOF has a pore size of from 0.3 to 2 nm, or from 0.4 to 1.9, or from 0.5 to 1.8 or from 0.6 to 1.7, or from 0.7 to 1.6, or about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9 or about 2.0 nm. In specific embodiments, the MOF is in the form of a powder having a Langmuir surface of at least 450 $m^2/g$ determined according to a 77K nitrogen gas isotherm fit to a Langmuir model. In a specific embodiment of this material, the material further comprising an adsorbed gas and particularly further comprises carbon dioxide.

In an embodiment, the invention provides a porous, metal-organic framework (MOF) material comprising zinc ions; an anionic compound selected from $[B_{12}H_{12}]^{2-}$, $[B_{12}F_{12}]^{2-}$, $[SiF_6]^{2-}$, $[PF_6]^-$, 1,2-dithiooxalic acid and its anions, 1,1-dithiooxalic acid and its anions, succinic acid and its anions, glutaric acid and its anions, adipic acid and its anions, 2-fluoroterephthalic acid and its anions, tetrafluorosuccinic acid and its anions, hexafluoroglutaric acid and its anions, octafluoroadipic acid and its anions; and a cycloazocarbyl compound. In an embodiment, the cycloazocarbyl compound is a 5-membered ring having 2, 3 or 4 nitrogen atoms. In an embodiment, the cycloazocarbyl compound is an imidazolate, triazolate or tetrazolate. In an embodiment, the cycloazocarbyl compound is a1,2,4-triazolate. In other embodiments, the cycloazocarbyl compound is selected from the group consisting of 1H-1,2,4-triazolate-1-carboxamidine, 3-amino-1,2,4-triazolate, imidazolate, 4-fluoroimidazolate, 2-methyl-imidazolate and 1,2,3,4-tetrazolate. In an embodiment, the cycloazocarbyl compound is a compound other than 3-amino-1,2,4-triazolate. More specifically the zinc ion is $Zn^{2+}$.

In an embodiment, the invention provides a metal-organic framework (MOF) comprising a plurality of cores, each core comprising a zinc ion coordinately bound to at least one at least bidentate cycloazocarbyl compound and at least one anionic compound selected from $[B_{12}H_{12}]^{2-}$, $[B_{12}F_{12}]^{2-}$, $[SiF_6]^{2-}$, $[PF_6]^-$, 1,2-dithiooxalic acid and its anions, 1,1-dithiooxalic acid and its anions, succinic acid and its anions, glutaric acid and its anions, adipic acid and its anions, 2-fluoroterephthalic acid and its anions, tetrafluorosuccinic acid and its anions, hexafluoroglutaric acid and its anions, octafluoroadipic acid and its anions, wherein the at least one at least bidentate cycloazocarbyl compound and the at least one said anionic compound is coordinately bound to the zinc ion of an adjacent core, wherein the plurality of linked cores defines pores within the framework. In an embodiment, the cycloazocarbyl compound is a 5-membered ring having 2, 3 or 4 nitrogen atoms. In an embodiment, the cycloazocarbyl compound is an imidazolate, triazolate or tetrazolate. In an embodiment, the cycloazocarbyl compound is a1,2,4-triazolate. In other embodiments, the cycloazocarbyl compound is selected from the group consisting of 1H-1,2,4-triazolate-1-carboxamidine, 3-amino-1,2,4-triazolate, imidazolate, 4-fluoroimidazolate, 2-methyl-imidazolate and 1,2,3,4-tetrazolate. In an embodiment, the cycloazocarbyl compound is a compound other than 3-amino-1,2,4-triazolate. More specifically the zinc ion is $Zn^{2+}$.

In an embodiment, the invention provides a material comprising at least one metal-organic framework (MOF) material, wherein the MOF material has pores and comprises zinc ions; an anionic compound selected from $[B_{12}H_{12}]^{2-}$, $[B_{12}F_{12}]^{2-}$, $[SiF_6]^{2-}$, $[PF_6]^-$, 1,2-dithiooxalic acid and its anions, 1,1-dithiooxalic acid and its anions, succinic acid and its anions, glutaric acid and its anions, adipic acid and its anions, 2-fluoroterephthalic acid and its anions, tetrafluorosuccinic acid and its anions, hexafluoroglutaric acid and its anions, octafluoroadipic acid and its anions; and a cycloazocarbyl compound. In an embodiment, the cycloazocarbyl compound is a 5-membered ring having 2, 3 or 4 nitrogen atoms. In an embodiment, the cycloazocarbyl compound is an imidazolate, triazolate or tetrazolate. In an embodiment, the cycloazocarbyl compound is a1,2,4-triazolate. In other embodiments, the cycloazocarbyl compound is selected from the group consisting of 1H-1,2,4-triazolate-1-carboxamidine, 3-amino-1,2,4-triazolate, imidazolate, 4-fluoroimidazolate, 2-methyl-imidazolate and 1,2,3,4-tetrazolate. In an embodiment, the cycloazocarbyl compound is a compound other than 3-amino-1,2,4-triazolate. More specifically the zinc ion is $Zn^{2+}$.

In an embodiment, the invention provides a method for preparing a porous metal organic framework (MOF) comprising at least an anionic compound selected from $[B_{12}H_{12}]^{2-}$, $[B_{12}F_{12}]^{2-}$, $[SiF_6]^{2-}$, $[PF_6]^-$, 1,2-dithiooxalic acid and its anions, 1,1-dithiooxalic acid and its anions, succinic acid and its anions, glutaric acid and its anions, adipic acid and its anions, 2-fluoroterephthalic acid and its anions, tetrafluorosuccinic acid and its anions, hexafluoroglutaric acid and its anions, and octafluoroadipic acid and its anions; and a cycloazocarbyl compound coordinated to at least one zinc ion, which comprises the step of combining a compound comprising zinc and a said anionic compound, and the cycloazocarbyl compound to form a reaction mixture; and reacting the compounds in the reaction mixture at a selected temperature. In an embodiment, the cycloazocarbyl compound is a 5-membered ring having 2, 3 or 4 nitrogen atoms. In an embodiment, the cycloazocarbyl compound is an imidazolate, triazolate or tetrazolate. In an embodiment, the cycloazocarbyl compound is a 1,2,4-triazolate. In other embodiments, the cycloazocarbyl compound is selected from the group consisting of 1H-1,2,4-triazolate-1-carboxamidine, 3-amino-1,2,4-triazolate, imidazolate, 4-fluoroimidazolate, 2-methyl-imidazolate and 1,2,3,4-tetrazolate. In an embodiment, the cycloazocarbyl compound is a compound other than 3-amino-1,2,4-triazolate. More specifically the zinc ion is $Zn^{2+}$.

The reacting step can be carried out in the presence of water, an organic solvent or a mixture thereof. In a specific embodiment, the solvent employed in the reaction is a mixture of water and organic solvent. In an embodiment, the mixture of water and organic solvent is miscible. In an embodiment, the organic solvent is or comprises an alcohol. In an embodiment the reacting step is carried out in the presence of water and at least one lower (C1-C4) alcohol. In an embodiment, the reacting step is carried out in the presence of water and an alcohol. In an embodiment, the ratio of water:alcohol (v/v) is between about 1:10 and 10:1. More specifically, the ratio of water:alcohol is or 1:10 and 5:1, or 1:5 and 4:1, or 1:4 and 3:1, or 1:4 and 2:1, of 1:3 and 2:1 or 1:3 and 1:1, or the ratio of water:alcohol (v/v) is about 5:6, or about 3:6, or about 2:3. In an embodiment, the alcohol is ethanol, propanol (various isomers including isopropanol) or butanol. In an embodiment, the alcohol is methanol and the ratio of water:methanol is 1:1 to 1:10 or more specifically 2:3 to 1:10. In specific embodiments, the reaction is carried out in the absence of water in methanol, ethanol, propanol or butanol (including isopropanol).

In specific embodiments, the method is carried out at a temperature in the range from 130° C. to 230° C. In specific embodiments, the temperature used in the method can range from 140° C. to 220° C., or 150° C. to 230° C., or 150° C. to 220° C., or 150° C. to 210° C., or 160° C. to 210° C., or 160° C. to 200° C., or 170° C. to 190° C. In other embodiment, the temperature employed is about 130° C., or about 140° C., or about 150° C., or about 160° C., or about 170° C., or about 180° C., or about 190° C., or about 200° C., or about 210° C., or about 220° C., or about 230° C. In an embodiment, the reaction mixture is formed at a mixing temperature that is less than the selected temperature. In an embodiment, the method further comprises the step of ramping the temperature from the mixing temperature to the selected temperature. In an embodiment, the ratio of the reaction time to the ramping time is at least 2, or is at least 3, or is at least 4, or is at least 5 or is at least 6.

In a specific embodiment the method comprises reaction of zinc oxalate with the anionic compound which can bind to the metal by coordination. In an embodiment, the reaction proceeds at atmospheric pressure. In an embodiment, the reaction proceeds with heating. In an embodiment, the reaction proceeds at a temperature of at least 80° C., or at least 90° C., or at least 100° C., or at least 110° C., or at least 120° C., or at least 130° C., or at least 140° C., or at least 150° C., or at least 160° C., or at least 170° C., or at least 180° C. In an embodiment, the reaction proceeds for at least 2 hours, or at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 hours. In an embodiment, the MOF material formed is subsequently treated with an organic solvent.

This porous MOF material can be employed in a method for the separation of carbon dioxide from a gas mixture containing carbon dioxide comprising the step of (a) contacting the gas mixture with at least one sorbent comprising this porous MOF material. In specific embodiment, the gas mixture contains in addition to carbon dioxide at least one gas selected from the group consisting of nitrogen, oxygen, methane, hydrogen, water vapor, carbon monoxide, hydrogen sulfide, sulfur dioxide, nitrogen dioxide, and any mixture of the foregoing. In specific embodiments the gas mixture contains at least two gases in addition to $CO_2$. In an embodiment, the gas mixture contains water vapor. In an embodiment, the gas mixture is selected from the group consisting of natural gas, air, shale gas, and flue gas. In an embodiment, the natural gas, air, shale gas, or flue gas contains water vapor.

In an embodiment, the porous metal-organic framework material is in the form of a powder. In an embodiment, the powder has a Langmuir surface of at least 450 $m^2/g$ determined according to the Langmuir sorption model applied to a nitrogen sorption isotherm at 77K.

In an embodiment of this method the contacting step is carried out at a temperature of from 50° C. to 200° C., or from 60° C. to 190° C., or from 70° C. to 180° C., or from 80° C. to 180° C., or from 90° C. to 180° C., or from 100° C. to 170° C., or at about 50, about 60, about 70, about 80, about 90, about 100, about 110, about 120, about 130, about 140, about 150, about 160, about 170, about 180, about 190 or 200° C.

In a specific embodiment of this method, the partial pressure of $CO_2$ in the gas ranges from 0.001 atm to 200 atm. In more specific embodiments, the partial pressure of $CO_2$ in the gas ranges from 0.01 to 200 atm, from 0.1 to 150 atm, from 0.1 to 100 atm, from 1 to 50 atm. In a more specific embodiment, the partial pressure of $CO_2$ in the gas ranges from 0.05 atm to 1 atm or 0.05 to 0.5 atm. In more specific embodiments, the partial pressure of $CO_2$ in the gas is about 0.001, about 0.01, about 0.1, about 1, about 10, about 20, about 30, about 40, about 50, about 60, about 70, about 80, about 90, about 100, about 110, about 120, about 130, about 140, about 150, about 160, about 170, about 180, about 190, about 200 atm, or an intermediate range between any of the foregoing.

This porous MOF material can be employed in a method of absorbing carbon dioxide, storing the carbon dioxide, or absorbing and storing the carbon dioxide, the method comprising contacting this porous material under conditions suitable for absorption of the carbon dioxide.

The MOF materials of this invention can be formed into granules having particle size ranging from 50 to 3000 nm and more specifically from 100-3000 nm. More specifically particle sizes of granules can range from 100-1000 nm. Methods are known in the art for forming powders into granules (granularization). In an embodiment, such methods comprise contacting the powder with a granularization liquid, for example a polymer in a suitable organic solvent under suitable conditions for formation of granules having the desired particle size. Granularization liquids may further comprise one or more surfactants. Methods useful for application to forming granules of MOF materials of this invention include those employing polysulfone [L. Li, J. Yao, P. Xiao, J. Shang, Y. Feng, P. A. Webley, H. Wang, Colloid Polym. Sci. 2013, 291, 2711-2717]; polylactic acid Q. Qian, X. Huang, X. Zhang, Z. Xie, Y. Wang, Angew. Chem., Int. Ed. 2013, 52, 10625-10629]; polyethylene glycol (e.g., PEG 6000) and/or polyvinylpyrrolidone (PVP) [T. Thirugnanam, Journal of Nanomaterials 2013. 10.1155/2013/362175]. Each of these references is incorporated by reference herein in its entirety for exemplary methods of granularization.

The MOF materials of the invention in powder or granular form are preferably activated prior to use for adsorbing $CO_2$. Methods for activating such materials are known in the art. In specific embodiment, the MOF materials of the invention are activated by heating under reduced pressure. More specifically, the MOF materials of this invention are activated by heating to a temperature of from about 100° C. to about 150° C. at a reduced pressure, e.g., $10^{-3}$ mbar or less, preferably $10^{-6}$ mbar. In an embodiment, MOF materials can be activated in a two-step heating process under reduced pressure (preferably $10^{-6}$ mbar) with a first step of heating to 60° C. for 2 hours followed by heating to 100° C. for 12 hours. Activation may be accomplished by heating at a controlled rate (e.g., 1° C./min) tone or more selected temperatures for a selected time. For example, the MOF can be activated by heating to 60° C. at 1° C./min for 2 hours followed by heating to 100° C. at 1° C./min for 12 hours. In another embodiment, the MOF materials are treated or washed with an organic solvent, such as acetone, prior to heating under educed pressure.

In specific embodiment, the MOF of this invention exhibits selectively for adsorption of $CO_2$ relative to adsorption of $N_2$. Selectively of adsorption can be assessed as illustrated in Vaidhyanathan R. et al. (2009) Chem. Comm. 5230-5232. In specific embodiments, the MOF of this invention designated CALF-20 (see the Example) exhibits selectivity for adsorption of $CO_2$ relative to $N_2$ of 10 fold or higher.

Vaidhyanathan R. et al. (2009) Chem. Comm. 5230-5232 and supplementary information available at www.rsc.ora/suppdata/cc/b9/b911481e/b911481e.pdf reports synthesis of a porous MOF comprising $Zn^{2+}$, oxalate and 3-amino-1,2,4-triazolate which can be used to adsorb $CO_2$. The MOF is described as having formula $Zn_2(C_2O_4)(C_2N_4H_3)_2 \cdot (H_2O)_{0.5}$. This material is designated CALF-15 herein. Each of these references is incorporated by reference herein for the description of the MOF material therein, as well as for details of methods for characterization of such MOF material, and further for comparison of properties with the MOF materials of this invention, specifically for comparison with the properties of CALF-20. For example, the $CO_2$ binding capacity of CALF-20 compared to that of CAFL-15 is 3.2 mmol/g vs. 2.5 mmol/g (at 0° C., 100 mbar $CO_2$ (~0.1 atm $CO_2$, ~10% $CO_2$). This represents a ~30% improvement of $CO_2$ binding capacity for CALF-20 compared to CALF-15.

The following references report metal-organic networks formed using 3-amino-1,2,4-triazolate-Y. Y. Lin, Y. B. Zhang, J. P. Zhang and X. M. Chen, Cryst. Growth Des., 2008, 8, 3673; H. Park, G. Krigsfeld, S. J. Teat and J. B.

Parise, Cryst. Growth Des., 2007, 7, 1343; W. Li, H. P. Jia, Z. F. Ju and J. Zhang, Cryst. Growth Des., 2006, 6, 2136; C. Y. Su, A. M. Goforth, M. D. Smith, P. J. Pellechia and H. C. zur Loye, J. Am. Chem. Soc., 2008, 130, 3576; and Z. Q. Zheng, C. W. Liu and B. Lin, Acta Crystallogr., Sect. E, 2007, 63, m1252-m1253. Most of the materials reported are either dense frameworks or have cages occupied by counter anions. Su et al. reported a microporous ZnFAtz compound, with amine-lined 1D pores. A zinc-triazolato-oxalate with 6-connected a-Po topology has been reported [Q.-G. Zhai, C.-Z. Lu, X.-Y. Wu and S. R. Batten, Cryst. Growth Des., 2007, 7, 2332] which has distinct properties and structure compared to the MOF materials of this invention. Each of these references is incorporated by reference herein in its entirety for the description of the materials therein for comparison of structure and properties of the materials therein with the materials of this invention.

Figure 6:
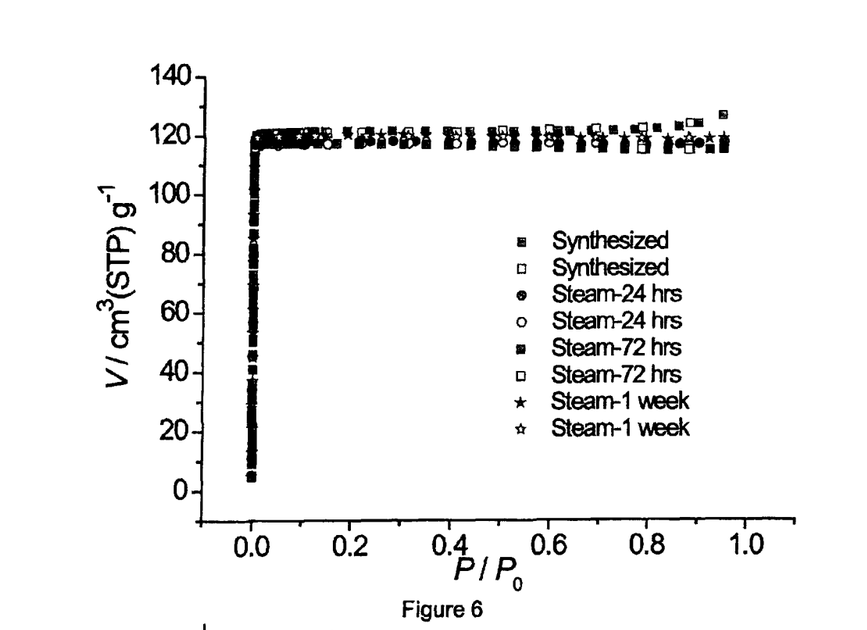
FIG. 6 shows $N_2$ sorption isotherms at −196° C. of the MOF material after steam treatment at 150° C. for 1, 3 and 7 days in comparison with the material prior to steam treatment.

In a specific embodiment, the MOF of this invention, particularly CALF-20, exhibit good stability to water as illustrated in FIG. 6.

The MOF of this invention can be subjected to a plurality of adsorption and desorption cycles with complete reversibility.

When a Markush group or other grouping is used herein, all individual members of the group and all possible combinations and subcombinations of the group are intended to be individually included in the disclosure. Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

THE EXAMPLES

A MOF having formula $Zn_2Tz_2Ox$ (Tz=1,2,4-triazolate, Ox=oxalate) was prepared in powdered form. Zinc oxalate (185 mg, 1.2 mmole) and 1,2,4-triazole (337 mg, 4.88 mmol) were added to water (4 mL) in a 23 mL Teflon™ liner for an autoclave. After about five minutes, methanol (6 mL) was added and mixture stirred for about an hour. The mixture was placed in an oven and the temperature ramped up to about 180° C. over a two hour period. The temperature was held at about 180° C. for about 48 hours, and then ramped down to ambient temperature over about 12 hours. The contents of the Teflon liner were filtered and washed with water (150-200 mL of water) taking care not to allow all the solid material to become dry. The material was washed with about 50-75 mL of methanol, and then vacuum filtered to dryness for about 20-30 minutes to obtain the powder. The material prepared by this method is designated CALF-20. FIG. 1 shows representative the X-ray diffraction pattern of two samples the material obtained using this method.

Figure 2:
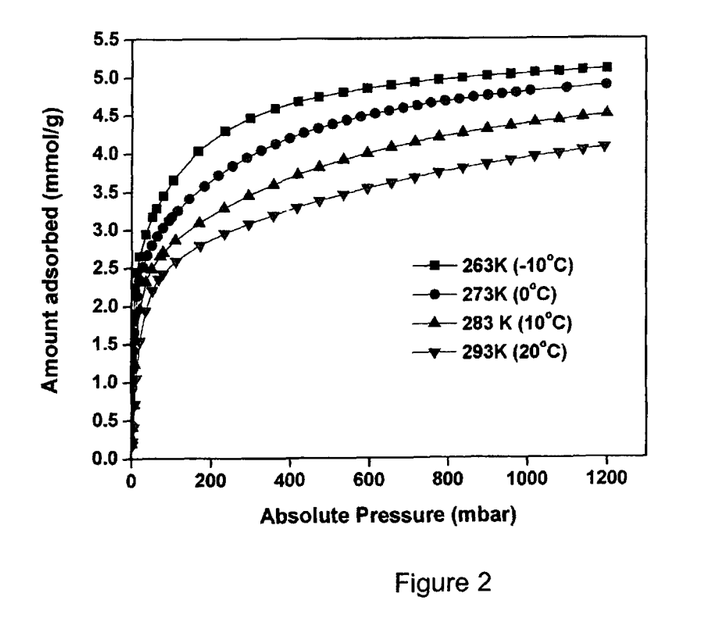
FIG. 2 shows low temperature $CO_2$ sorption isotherms for the MOF material obtained as described in the Example.
Figure 3:
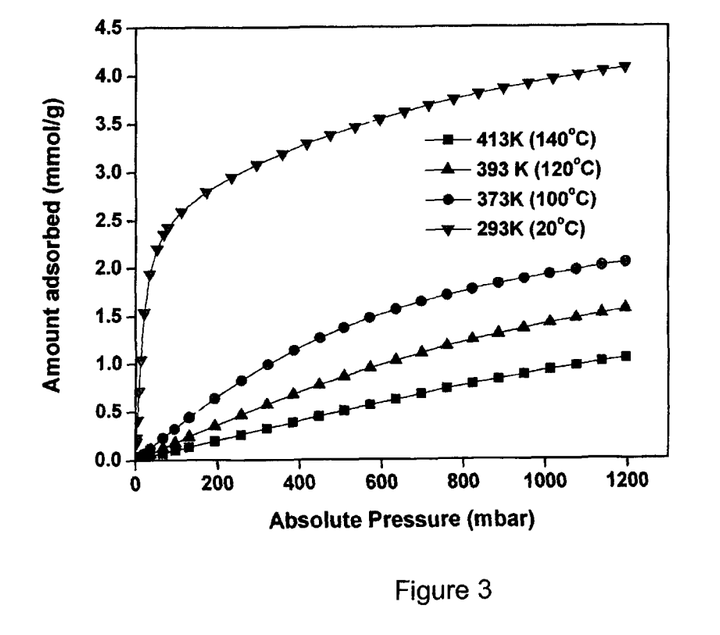
FIG. 3 shows high temperature $CO_2$ sorption isotherms for the MOF material obtained as described in the Example.

The adsorption isotherms of carbon dioxide were determined at different temperatures using CALF-20. FIGS. 2 and 3 show the isotherms of carbon dioxide, the adsorbed amounts of the gas being given in mmol/g of the material.

Figure 4:
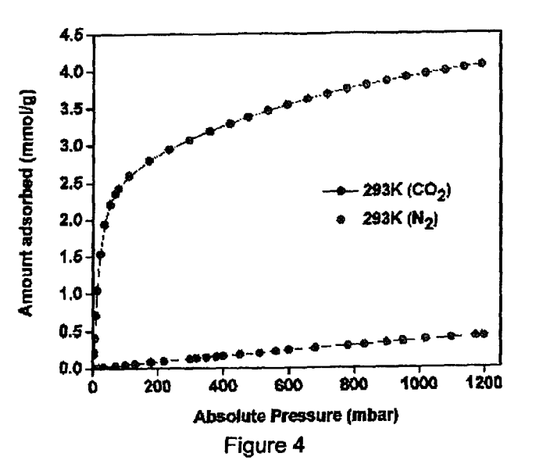
FIG. 4 is a comparison of $CO_2$ versus $N_2$ uptake of at 0° C. isotherms for the MOF material obtained as described in the Example.

The adsorption isotherms of the carbon dioxide and nitrogen were determined at different temperatures using CALF-20, with results obtained shown in FIG. 4.

As can be seen from the figures, the results obtained establish the feasibility of separating carbon dioxide from a gas mixture containing at least nitrogen by contacting a mixture of the gases with MOF material of the invention.

Figure 5:
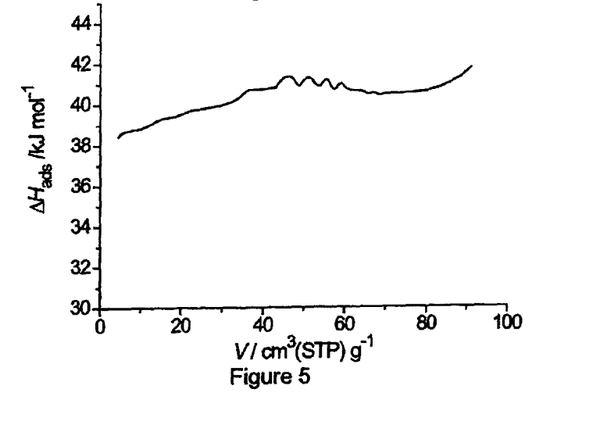
FIG. 5 shows isosteric heat of adsorption for $CO_2$ in the MOF material obtained as described in the Example.

The affinity of a particular gas for a MOF material can be determined by measuring the isosteric heat of adsorption at zero coverage. The results exemplified by FIG. 5 show that a column made of the porous material of the invention is capable of adsorbing carbon dioxide. A MOF may be specifically designed to have a disproportionately high selectivity or affinity for a particular component of a mixture, particularly carbon dioxide, relative to other gases of a gaseous mixture.

Figure 7:
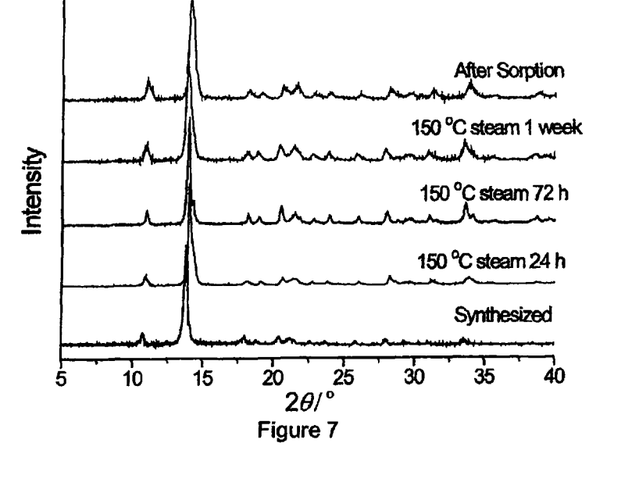
FIG. 7 shows the X-ray diffraction patterns of the MOF material after steam treatment at 150° C. for 1, 3 and 7 days in comparison with the material prior to exposure and after sorption.

Hydrolytic stability of the MOF material was tested. 100 mg of the material in a glass vial was placed in a Teflon-lined reactor, in which 5 mL pure water was added outside the vial. The reactor was heated at 150° C. for 24, 72 hours and 1 week. Results are shown in FIG. 6. Nitrogen sorption is more sensitive to microstructure than $CO_2$ sorption and the isotherms obtained after this steam treatment show the capacity and internal surface area of the MOF are retained. Given that moisture is present in a flue gas and that steam is a significant route to regenerate the sorbent, this stability is significant and atypical of MOFs. One can also see from FIG. 7 that the PXRDs of the materials taken after the various heat-exposure times that the MOF retains its structure i.e., is thermally and hydrolytically stable under the conditions tested.

The specific surface area of native and steam-treated samples, as calculated using the Langmuir model is shown in Table 1.

TABLE 1

|  | Synthesized | Steam 24 hours | Steam 72 hours | Steam 1 week |
| --- | --- | --- | --- | --- |
| Saturation sorption ($cm^3/g$) | 121 | 118 | 117 | 117 |
| Langmuir surface area ($m^2/g$) | 528 | 512 | 507 | 522 |

The invention claimed is:

1. A material comprising at least one metal-organic framework (MOF), wherein the MOF has pores and comprises zinc ions, oxalate, and a cycloazocarbyl compound other than 3-amino-1,2,4-triazolate, wherein the MOF, when in the form of a powder, has a Langmuir surface area of at least 450 $m^2/g$ determined according to a 77K nitrogen gas isotherm fit to a Langmuir model.

2. The material of claim 1, wherein the ring of the cycloazocarbyl compound is a 5-membered ring having 2, 3 or 4 nitrogen atoms.

3. The material of claim 1, wherein the cycloazocarbyl compound is an imidazolate, triazolate or tetrazolate.

4. The material of claim 1, wherein the cycloazocarbyl compound is selected from the group consisting of 1H-1,2,4-triazolate-1-carboxamidine, imidazolate, 4-fluoroimidazolate, 2-methyl-imidazolate and 1,2,3,4-tetrazolate.

5. The material of claim 1, wherein the cycloazocarbyl compound is 1H-1,2,4-triazolate-1-carboxamidine, or 1,2,4-triazolate.

6. The material of claim 1, wherein the zinc ion is $Zn^{2+}$.

7. The material of claim 1, wherein the MOF has a pore size of from 0.3 to 2 Nm, or from 0.4 to 1.9, or from 0.5 to 1.8, or from 0.6 to 1.7, or from 0.7 to 1.6, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9 or about 2.0 Nm.

8. The material of claim 1, wherein the cycloazocarbyl compound is 1,2,4-triazolate and the MOF has a powder X-ray diffraction pattern having the highest intensity diffraction peak in the range $10°<2\theta<15°$ with Cu Kα radiation.

9. The material of claim 1, wherein the MOF has the PXRD pattern substantially as shown in FIG. 1.

10. The material of claim 1, further comprising an adsorbed gas.

11. The material of claim 10, wherein the gas is carbon dioxide.

12. A metal-organic framework (MOF) comprising a plurality of cores, each core comprising a zinc ion coordinately bound to at least one at least bidentate cycloazocarbyl compound and at least one oxalate, wherein the at least one at least bidentate cycloazocarbyl compound and the at least one oxalate is coordinately bound to the zinc ion of an adjacent core, wherein the plurality of linked cores defines pores within the framework, wherein the cycloazocarbyl compound is other than 3-amino-1,2,4-triazolate, and wherein the MOF, when in the form of a powder, has a Langmuir surface area of at least 450 $m^2/g$ determined according to a 77K nitrogen gas isotherm fit to a Langmuir model.

13. The MOF of claim 12, wherein there are two said at least bidentate cycloazocarbyl compounds coordinately bound to the zinc ion of each said core.

14. The MOF of claim 13, wherein there are two carboxylate oxygens of said oxalate coordinately bound to the zinc ion of each core.

15. The MOF of claim 14, wherein the two carboxylate oxygens are covalently bound to vicinal carbon atoms of the oxalate.

16. The MOF of claim 15, wherein the other of the two carboxylate oxygens are coordinately bound to the zinc ion of an adjacent core.

17. The MOF of claim 12, wherein the cycloazocarbyl compound is tridentate and each cycloazocarbyl compound is coordinately bound to zinc ions of three adjacent cores.

18. The MOF of claim 12, wherein the cycloazocarbyl compound is 1,2,4-triazolate.

19. The MOF of claim 12, further comprising an adsorbed species.

20. The MOF of claim 19, wherein the adsorbed species is carbon dioxide.

21. The MOE of claim 12 comprising a core of formula I:

wherein each $M^1$, $M^2$ and $M^3$ is $Zn^{2+}$;
$XR^1$ is selected from the group consisting of N and $CR^3$;
and at least one of $R^2$ and $R^3$ is H, and the other of $R^2$ and $R^3$ is selected from the group consisting of H, —$NH_2$, optionally substituted ($C_1$-$C_{10}$)alkyl, optionally substituted ($C_1$-$C_{10}$)alkenyl, optionally substituted ($C_1$-$C_{10}$)

alkynyl, optionally substituted ($C_1$-$C_{10}$)heteroalkyl, optionally substituted ($C_1$-$C_{10}$)heteroalkenyl, optionally substituted ($C_1$-$C_{10}$)heteroalkynyl, optionally substituted cycloalkyl, optionally substituted cycloalkenyl, optionally substituted aryl, optionally substituted heterocycle, wherein when X is C—$NH_2$, then $R_2$ is a group other than hydrogen.

22. The MOF of claim 21, wherein the core is of formula II:

wherein, for each Y-$L^1$-Y, Y-$L^2$-Y and Y-$L^3$-Y,
(i) Y is an oxygen atom, and each $L^1$, $L^2$ and $L^3$ is independently selected from the group consisting of —C(O)C(O)—, —C(S)C(S)—, —C(O)$CH_2CH_2$C(O)—, —C(O)$(CH_2)_3$C(O)—, —C(O)$(CH_2)_4$C(O)—, —C(O)$CF_2CF_2$C(O)—, —C(O)$(CF_2)_3$C(O)—, —C(O)$(CF_2)_4$C(O)—, and or
(ii) one, two or three of Y-$L^1$-Y, Y-$L^2$-Y and Y-$L^3$-Y is —SC(O)C(O)S— Y and the other of Y-$L^1$-Y, Y-$L^2$-Y and Y-$L^3$-Y is as defined in paragraph (i).

23. The MOF of claim 22, wherein the core is of formula Ill:

wherein each Z is, independently of each other Z, as defined for Y-$L^1$-Y in paragraph (i) or (ii) in which the atom represented by a first Y thereof is coordinated to $M^1$, $M^2$ and $M^3$, respectively, and the atom represented by the second Y is coordinated to a metal atom of an adjacent core of the MOF.

24. The MOF of claim 23, wherein each of $M^1$, $M^2$ and $M^3$ is further coordinated to first and second nitrogen atoms in the rings of first and second neighboring polyazolate groups, a polyazolate being a cycloazocarbyl molecule containing three or four nitrogen atoms in its ring, and taking the form of a triazolate or tetrazolate as a constituent of a MOF.

25. A porous, metal-organic framework (MOF) material comprising zinc ions, oxalate, and a cycloazocarbyl compound wherein the cycloazocarbyl compound is other than 3-amino-1,2,4-triazolate, wherein the MOF when in the form of a powder, has a Langmuir surface area of at least 450 $m^2$/g determined according to a 77K nitrogen gas isotherm fit to a Langmuir model.

26. A material comprising at least one metal-organic framework (MOF) material of claim 25.

27. A method for preparing a porous metal organic framework (MOF) comprising at least an oxalate and a cycloazocarbyl compound coordinated to at least one zinc ion, which comprises the step of combining a zinc oxalate compound and the cycloazocarbyl compound to form a reaction mixture; and reacting the compounds in the reaction mixture at a selected temperature, with the exception that the cycloazocarbyl compound is not 3-amino-1,2,4-triazolate, wherein the reacting step is carried out in a C1-C4 alcohol or in a mixture of a C1-C4 alcohol and water.

28. The method of claim 27, wherein the alcohol is ethanol or isopropanol.

29. The method of claim 27, wherein the reacting step is carried out in a mixture of a C1-C4 alcohol and water.

30. The method of claim 29, wherein the reacting step is carried out in a mixture of water and methanol, wherein the ratio of water:methanol (v/v) is between about 1:10 and 10:1, or 1:10 and 5:1, or 1:5 and 4:1, or 1:4 and 3:1, or 1:4 and 2:1, of 1:3 and 2:1 or 1:3 and 1:1, or the ratio of water:methanol (v/v) is about 5:6, or about 3:6, or about 2:3.

31. The method of claim 30 wherein the ratio of water:methanol ranges from 1:1 to 1:10.

32. The method of claim 27, wherein the selected temperature is in the range from 130° C. to 230° C., or is in the range or 140° C. to 220° C., or 150° C. to 230° C., or 150° C. to 220° C., or 150° C. to 210° C., or 160° C. to 210° C., or 160° C. to 200° C., or 170° C. to 190° C., or is about 130° C., or about 140° C., or about 150° C., or about 160° C., or about 170° C., or about 180° C., or about 190° C., or about 200° C., or about 210° C., or about 220° C., or about 230° C.

33. The method of claim 27, wherein the cycloazocarbyl compound is selected from an imidazole, a triazole or a tetrazole.

34. The method of claim 27, wherein the cycloazocarbyl compound is a 1,2,4-triazole.

35. The method of claim 27, wherein the cycloazocarbyl compound is 1,2,4-triazole.

36. The method of claim 27, wherein after the reaction, the MOF material formed is heated to a temperature between 100-150° C. under reduced pressure.

37. A method for the separation of carbon dioxide from a gas mixture containing carbon dioxide comprising the step of (a) contacting the gas mixture with at least one sorbent comprising a porous MOF material of claim 1.

38. The method of claim 37, wherein the gas mixture contains in addition to carbon dioxide at least one gas selected from the group consisting of nitrogen, oxygen, methane, hydrogen, water vapor, carbon monoxide, hydrogen sulfide, sulfur dioxide, nitrogen dioxide, and any mixture of the foregoing.

39. The method of claim 38, wherein the gas mixture contains at least two additional gases.

40. The method of claim 37, wherein the gas mixture is selected from the group consisting of natural gas, air, shale gas, and flue gas.

41. The method of claim 37, wherein the gas mixture contains water vapor.

42. The method of claim 37, wherein step (a) is carried out at a temperature of from 50° C. to 200° C., or from 60° C. to 190° C., or from 70° C. to 180° C., or from 80° C. to 180° C., or from 90° C. to 180° C., or from 100° C. to 170° C., or at about 50, about 60, about 70, about 80, about 90, about 100, about 110, about 120, about 130, about 140, about 150, about 160, about 170, about 180, about 190 or 200° C.

43. A method of absorbing carbon dioxide, storing the carbon dioxide, or absorbing and storing the carbon dioxide, the method comprising the separation method of claim 37.

44. A porous, metal-organic framework (MOF) material comprising zinc ions; an anionic compound selected from $[B_{12}H_{12}]^{2-}$, $[B_{12}F_{12}]^{2-}$, $[SiF_6]^{2-}$, $[PF_6]^-$, 1,2-dithiooxalic acid and its anions, 1,1-dithioxalic acid and its anions, glutaric acid and its anions, anions, 2-fluroterephralic acid and its anions, tetrafluorosuccinic acid and its anions, hexafluoroglutaric acid and its anions, octafluoroadipic acid and its anions; and a cycloazocarbyl compound, wherein when in the form of a powder, the MOE has a Langmuir surface area of at least 450 m$^2$/g determined according to a 77K nitrogen gas isotherm fit to a Langmuir model.

45. A material comprising at least one metal-organic framework (MOF) material of claim 44.

\* \* \* \* \*

UNITED STATES PATENT AND TRADEMARK OFFICE
CERTIFICATE OF CORRECTION

PATENT NO. : 9,782,745 B2
APPLICATION NO. : 14/775267
DATED : October 10, 2017
INVENTOR(S) : George Shimizu et al.

Page 1 of 1

It is certified that error appears in the above-identified patent and that said Letters Patent is hereby corrected as shown below:

In the Claims

At Column 16 Line 49 (Claim 21), replace "MOE" with --MOF--.

At Column 19 Line 15 (Claim 44), replace "its anions, anions, 2-fluroterephralic" with --its anions, 2-fluroterephralic--.

At Column 19 Line 19 (Claim 44), replace "MOE" with --MOF--.

Signed and Sealed this
Tenth Day of April, 2018

Andrei Iancu
*Director of the United States Patent and Trademark Office*